United States Patent
Schmitt

(10) Patent No.: US 11,864,830 B2
(45) Date of Patent: Jan. 9, 2024

(54) LITHOTRIPSY SYSTEMS WITH DISPERSED LASER NODES

(71) Applicant: GYRUS ACMI, INC., Westborough, MA (US)

(72) Inventor: Jeffrey M. Schmitt, Bolton, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 203 days.

(21) Appl. No.: 17/336,496

(22) Filed: Jun. 2, 2021

(65) Prior Publication Data

US 2021/0401499 A1 Dec. 30, 2021

Related U.S. Application Data

(60) Provisional application No. 63/043,310, filed on Jun. 24, 2020.

(51) Int. Cl.
| | | |
|---|---|---|
| *A61B 18/20* | (2006.01) | |
| *A61B 18/26* | (2006.01) | |
| *A61B 17/221* | (2006.01) | |
| *A61B 17/00* | (2006.01) | |

(52) U.S. Cl.
CPC ............ *A61B 18/26* (2013.01); *A61B 17/221* (2013.01); *A61B 2017/0034* (2013.01); *A61B 2018/208* (2013.01)

(58) Field of Classification Search
CPC ................................ A61B 18/20; A61B 18/26
See application file for complete search history.

(56) References Cited

U.S. PATENT DOCUMENTS

| 6,264,664 | B1 | 7/2001 | Avellanet | |
|---|---|---|---|---|
| 6,511,485 | B2 | 1/2003 | Hirt et al. | |
| 6,533,792 | B2 | 3/2003 | Menne et al. | |
| 2005/0033313 | A1* | 2/2005 | Chu ................ | A61B 17/221 606/114 |
| 2005/0154378 | A1* | 7/2005 | Teague ............ | A61B 17/221 606/2.5 |

(Continued)

FOREIGN PATENT DOCUMENTS

| CN | 115734760 A | 3/2023 |
|---|---|---|
| WO | WO-2021262404 A1 | 12/2021 |

OTHER PUBLICATIONS

"Nitinol Stone Retrieval Basket", Escape-Boston Scientific, [Online]. Retrieved from the Internet: <URL: https://www.bostonscientific.com/content/gwc/en-US/products/retrieval-devices/escape.html>, (Accessed Apr. 8, 2020), 3 pgs.

(Continued)

*Primary Examiner* — Lynsey C Eiseman
(74) *Attorney, Agent, or Firm* — Schwegman Lundberg & Woessner, P.A.

(57) ABSTRACT

A laser lithotripsy system to deliver laser energy from one or more laser sources to a stone (e.g., mobile calculus), the system including a capture portion, a first laser node and a second laser node. The capture portion configured to be movable from a stored state to a deployed state. In the deployed state, the capture portion is configured to at least partially surround the stone. The first laser node and the second laser node are coupled to the capture portion and are configured to deliver the laser energy to the stone, and the first laser node is spaced apart from the second laser node.

25 Claims, 8 Drawing Sheets

(56) References Cited

U.S. PATENT DOCUMENTS

| | | | |
|---|---|---|---|
| 2010/0137847 A1* | 6/2010 | Cecchetti | A61B 18/26 606/2.5 |
| 2019/0117309 A1 | 4/2019 | Shelton | |
| 2020/0054397 A1 | 2/2020 | Brown et al. | |
| 2020/0129195 A1 | 4/2020 | Mcgowan et al. | |

OTHER PUBLICATIONS

"Stone Retrieval Guide", Boston Scientific, (2018), 2 pgs.

Wilson, CR, et al., "(Abstract) A Miniaturized, 1.9F Integrated Optical Fiber and Stone Basket for Use in Thulium Fiber Laser Lithotripsy", PubMed. J Endourol, [Online]. Retrieved from the Internet: <URL: https://www.ncbi.nlm.nih.gov/pubmed/26167738>, (Oct. 29, 2015), 1 pg.

"International Application Serial No. PCT/US2021/035342, International Preliminary Report on Patentability dated Jan. 5, 2023", 7 pgs.

"International Application Serial No. PCT/US2021/035342, International Search Report dated Sep. 15, 2021", 5 pgs.

"International Application Serial No. PCT/US2021/035342, Written Opinion dated Sep. 15, 2021", 6 pgs.

* cited by examiner

LITHOTRIPSY SYSTEMS WITH DISPERSED LASER NODES

CROSS-REFERENCE TO RELATED APPLICATION

This application claims the benefit of priority to U.S. Provisional Patent Application Ser. No. 63/043,310 filed Jun. 24, 2020, the contents of which are incorporated herein by reference in their entirety.

TECHNICAL FIELD

The present document relates to techniques for breaking obstructions, such as physiological calculi or "stones" using lithotripsy, and more particularly to techniques for breaking the obstructions using laser lithotripsy.

BACKGROUND

Medical endoscopes were first developed in the early 1800s and have been used to inspect inside the body. A typical endoscope consists of a distal end comprising an optical or electronic imaging system and a proximal end with controls for manipulating the tools and devices for viewing the image, with a solid or tubular elongate shaft connecting the ends. Some endoscopes allow a physician to pass tools or treatments down one or more hollow working channels, for example, to resect tissue or retrieve objects.

Over the past several decades, several advances have been made in the field of endoscopy, and in particular relating to the breaking up of physiologic calculi in the bile ducts, urinary tract, kidneys, and gall bladder. Physiological calculi in these regions may block ducts and cause a patient a substantial amount of pain and therefore must be broken down and/or removed. Different techniques have been developed to break up stones, including ultrasonic lithotripsy, pneumatic lithotripsy, electro-hydraulic lithotripsy (EHL), and laser lithotripsy including dissolution of calculi using green light, YAG, or holmium lasers.

OVERVIEW

The present inventor has recognized, among other things, that problems to be solved in performing laser lithotripsy in a living being include a surgeon being able to easily capture, fragment and remove the fragments of a stone located within the body. The present subject matter can provide solutions to these problems and other problems.

This disclosure describes laser lithotripsy systems including a deployable, expandable capture portion having integrated laser nodes that are dispersed across a surface of the capture portion. The capture portion can be provided, for example, in the form of a bag, basket or scaffold. The deployable capture portion can enable a surgeon to capture a stone and ablate the stone using a minimally invasive approach, such as ureteroscopy or percutaneous nephrolithotomy (PCNL). Aspects of the laser lithotripsy system described herein can be used with an endoscope, such as a ureteroscope or a nephroscope, or can be used with a separate flexible, semi-rigid, or rigid instrument or device.

The laser nodes can direct laser energy received from at least one laser source, such as via one or more laser fibers, to multiple locations on the exterior surface of a stone. In some examples, the laser nodes can direct laser energy to the stone concurrently. In some examples, the dispersed nature of the laser nodes enables selective, targeted application of energy. For example, laser energy can be applied on only one side or to one section, or certain sections of a stone, depending on the characteristics of the stone. This targeted application of energy can be accomplished by activating a subset of the plurality of laser nodes across a network of nodes.

This disclosure also describes a capture portion having an opening to receive a stone. In some examples, the opening can be closed to capture the stone therein. The capture portion can be used together with the laser nodes, but also has applications separate from the laser nodes.

This overview is intended to provide an overview of subject matter of the present patent application. It is not intended to provide an exclusive or exhaustive explanation of the invention. The detailed description is included to provide further information about the present patent application.

Figure 1:
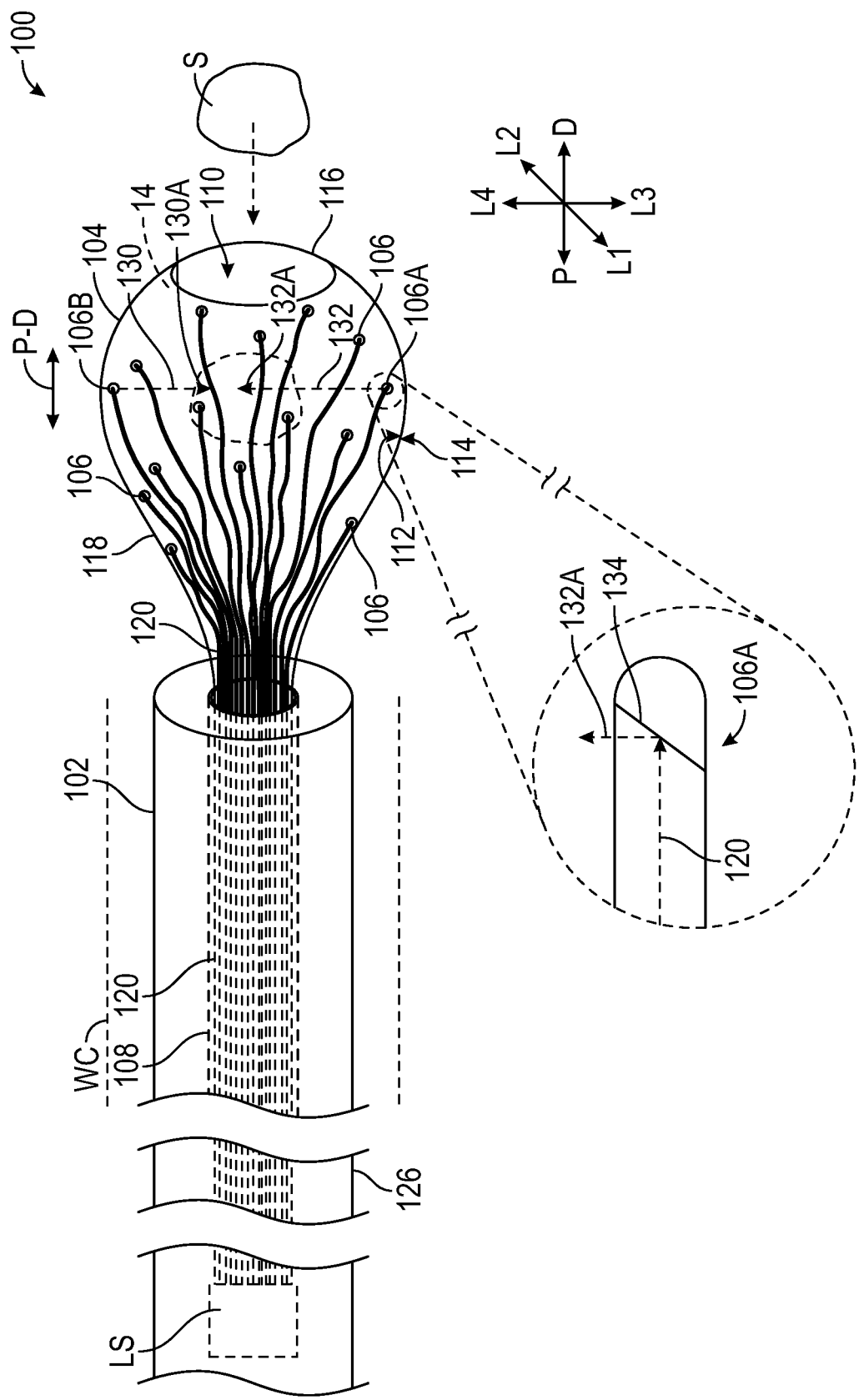
FIG. 1 illustrates a side view of a portion of a lithotripsy system, in accordance with at least one example.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure provides examples of systems and methods that can help address the problem of fragmenting and collecting stones during lithotripsy, such as laser lithotripsy or other surgeries or treatments. Laser lithotripsy uses an optical transmission media or optical pathway such as one or more laser fibers to transmit laser energy from at least one laser source to a target obstruction, such as a stone.

Fragmenting and collecting stones can be challenging because the stones can be free-floating, mobile calculi. Because the stones are generally not restrained by an attachment to tissue and are free-floating, they may move during the process of fragmenting. Another challenge is that the stones can have varying hardness throughout different portions of the stone and some portions of the surface of the stone may be easier to break through than others. Stones can be present in various organs of the body, including, but not limited to kidney, bladder, ureter, bile ducts and gallbladder.

Benefits of the approaches described herein include, among other things, capturing the stone for treatment, communicating laser energy to the stone from multiple spaced apart laser nodes to ablate the stone. Communicating the laser energy to multiple locations across the surface of the stone versus the current application of energy focally applied at only one point at any given time can increase stone ablation speed, which can reduce procedure time. This dispersed application of laser energy can also aid in breaking through a generally harder outer layer of a stone. Further, because the laser energy is directed inward toward the kidney stone, adjacent tissue can be avoided.

This disclosure also provides solutions to the problem of capturing the stone for treatment and maintaining capture of the stone fragments for removal that can be used with other forms of lithotripsy or other procedures for capturing stones or tissue in vivo. Deployable capture portions, such as a bag, basket, scaffold, pinchers, grasping fingers or receptacle can capture the stone and hold the stone during treatment, as well as maintain capture of the fragmented stone for removal. This can lead to shorter procedure times because the position of the stone is controlled and known during the lithotripsy process, reducing retropulsion and other unwanted movement of the stone which can lead to a surgeon having to "chase" the stone throughout the procedure. Maintaining capture of the stone fragments can also improve the post-procedure stone free rate in a patient.

For the purposes of this disclosure, "proximal" refers to an end of the system that is closer the device operator during use, and "distal" refers to an end of the system that is distal, or further from the device operator during use.

FIG. 1 shows a side view of an example of portions of a laser lithotripsy system 100. The lithotripsy system 100 can include or can be coupled to at least one laser source LS. The lithotripsy system 100 can be introduced into a patient via a working channel WC of an endoscope or similar instrument. The laser source LS can include one or more of a diode or a diode-pumped thulium fiber laser, holmium laser, green light laser, YAG laser, or another laser configured to deliver laser energy.

The laser lithotripsy system 100 can include a sheath 102, a capture portion 104 and a plurality of laser nodes 106. The capture portion 104 can serve as a stone retention member configured to be movable from a stored state housed within a lumen 108 of the sheath (e.g., elongate tube) to a deployed state to capture a stone S. The sheath 102 can have any suitable cross section, including but not limited to: circular, oval, elliptical, polygonal or irregular.

The capture portion 104 is shown in the deployed state and the direction of movement from the stored state to the deployed state and vice-versa is shown by movement arrow P-D. A deployed state can refer to a state in which the capture portion 104 is expanded and/or advanced distal of the sheath 102. Movement from the stored state to a deployed state can include movement of the capture portion 104 in a distal direction D, as well as expansion in a lateral direction, such as but not limited to lateral directions L1, L2, L3, L4. In other words, deployment can include the capture portion 104 being movable in a direction having a longitudinal component along the proximal-distal direction and a lateral component relative to the sheath 102 when actuated by an operator. An example of stored and deployed states, are shown and described in additional detail in the example of FIGS. 5A and 5B.

To receive the stone S, the capture portion 104 can include a receiving cavity 110. The receiving cavity 110 can have an inner surface 112 and an outer surface 114 configured to at least partially surround the stone S. In the deployed state, the capture portion 104 can be configured to receive the stone S into the receiving cavity 110 through an opening 116. In some examples, the capture portion 104 can include a layer 118 of compliant material such as a mesh. The mesh can include, but is not limited to, the type of meshes that are used in hernia and other tissue repair procedures. Various examples of openings are described herein, including openings that remain open, or openings that can be opened/and or at least partially closed by an operator.

At least one laser node 106 can be coupled to the capture portion 104 to receive laser energy from the laser source LS and to distribute the laser energy to the stone S. The example of FIG. 1 illustrates a plurality of laser nodes 106 including a first laser node 106A and a second laser node 106B located in a spaced apart arrangement, as well as other similar laser nodes. The first and second laser nodes 106A, 106B can be configured to direct the laser energy inward from the capture portion 104 towards the receiving cavity 110. Any of the laser nodes 106 may be a side-firing type laser node in order to direct the laser energy into the receiving cavity. In this arrangement, the laser energy received from the at least one laser source LS can be delivered to different parts of the stone S by different laser nodes 106 via at least one laser fiber 120. For example, the laser energy can be delivered to multiple, spaced apart locations on the stone S, such as a first location 130A and a second location 132B. Aspects of spaced apart laser nodes are described in further detail with respect to at least FIG. 5.

Figure 3:
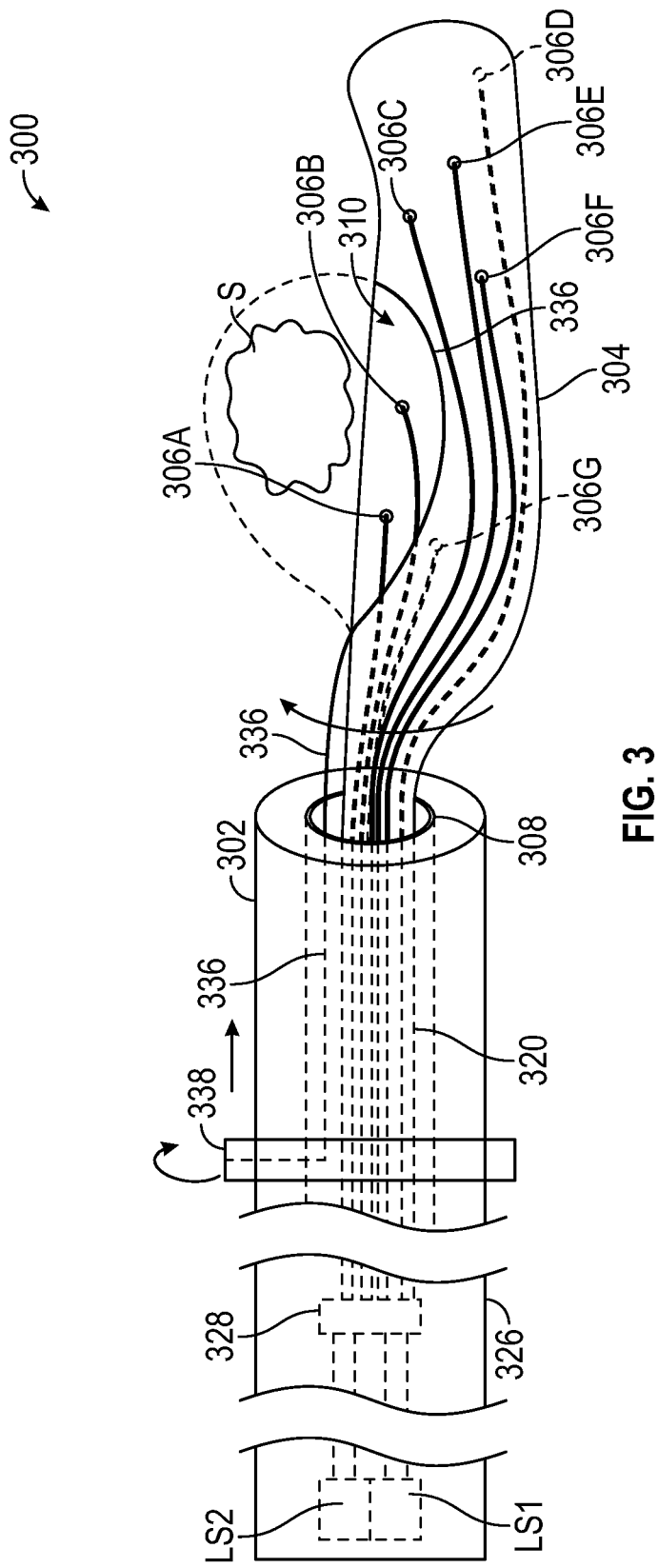
FIG. 3 illustrates a side view of a portion of a third lithotripsy system, in accordance with at least one example.

The laser energy can be delivered from the laser source LS to the laser nodes 106 via at least one laser fiber 120. A laser coupling 126 can be located between the at least one laser source LS and at least one laser node 106. The laser coupling 126 can couple the laser energy from the at least one laser source LS to the laser nodes 106 in any suitable manner to provide laser energy to the laser nodes 106 to fragment a stone S, such as via the at least one fiber 120. For example, as shown in FIG. 1, the laser coupling 126 can include laser fibers 120, each being individually connected to the laser source LS. Or, as shown in FIG. 3, the laser coupling 326 can include a common manifold 328 connection where the laser energy produced by the at least one laser source (shown as a first and second laser source, LS1 and LS2) can be divided into portions of laser energy to be delivered to each of the laser nodes 306 (FIG. 3). Any suitable laser coupling or manifold including combinations of any of the laser couplings described herein can be provided to deliver laser energy to the laser nodes 106. Thus, regardless of the particular characteristics of the laser coupling 126 or manifold 128, a first portion of the laser energy generated by the at least one laser source LS can be delivered to the first laser node 106A and a second portion of the laser energy generated by the at least one laser source LS can be delivered to the second laser node 106B.

By spacing-apart or dispersing multiple laser nodes 106 along the capture portion 104, the application of energy from different directions can help to keep the stone S in place.

This can be particularly helpful when the laser energy is applied to the stone S in a generally equal and opposite manner. When laser energy is applied to a stone S, bubbles can be generated in the fluid contributing to retropulsion. By applying laser energy from opposite directions, even if not exactly equal and exactly opposite, a reduction in retropulsion can be obtained over a traditional lithotripsy system that applies the laser energy to a single focal point on the stone S.

In an example, FIG. 1 shows the first laser node 106A delivering at least a portion of the laser energy to the stone S along a first path 130 to a first location 130A, and the second laser node 106B delivering at least a portion of the laser energy to the stone S along a second path 132 to a second location 132A. Any number of laser nodes 106 that provide respective portions of the laser energy can be provided. The portion of the laser energy can be described as a first laser beam, and the second portion of the laser energy can be described as a second laser beam. In some examples, the sum of all the portions of the laser energy (e.g., sum of all the laser beams communicated by the laser nodes 106) can equal the total laser energy received from or produced by the laser source LS.

Another benefit of multiple, spaced apart laser nodes 106 is that the laser energy can be delivered to the stone S with the added benefit of dispersing the heat of the laser energy through a greater portion of the fluid surrounding the stone S. Laser energy can heat fluid in and adjacent to the path the laser energy travels. By delivering the laser energy through different paths in the fluid, such as a first path 130 and a second path 132, instead of a single path, the same or more laser energy can be applied to the stone S while reducing localized heat in any particular portion of the fluid, keeping the fluid cooler.

The total energy received from the laser source LS can be portioned (e.g., divided) into a first portion of laser energy and a second portion of the laser energy. Depending on the locations of the first and second nodes 106, retropulsion can be reduced because a first force on the stone S as a result of the first portion of the laser energy communicated from the first laser node 106A to the first location 130A can cancel out at least portion of a second force on the stone S as a result of the second portion of the laser energy communicated from the second laser node 106B to the second location 132A. The laser nodes 106 can direct laser energy to multiple points on the exterior surface of a stone S concurrently or in a staggered or serial manner.

FIG. 1 also shows a close-up view of the first laser node 106A. Other laser nodes 106 may be the same as or similar to the first laser node 106A. The first laser node 106A can include a side firing laser. In other words, the distal end portion of first laser node 106A can be configured to one or more of: deflect, reflect, refract or diffract the first portion of the laser energy. The first laser node 106A can include a distal end portion having a deflector 134 configured to deflect the first portion of the laser energy received from the laser source LS towards the receiving cavity 110 (e.g., first laser beam along first path 130), and thereby towards a stone S captured within the receiving cavity 110. The deflector 134 can include a first reflective surface, mirror or other reflective/deflective means to cause the first portion of the laser energy to be communicated into the receiving cavity 110. In another example, the geometry of the laser fiber 120 can include an angled surface that serves as the deflector 134 causing the laser energy to outcouple from the laser node 106A at an angle towards the receiving cavity 110.

Figure 2:
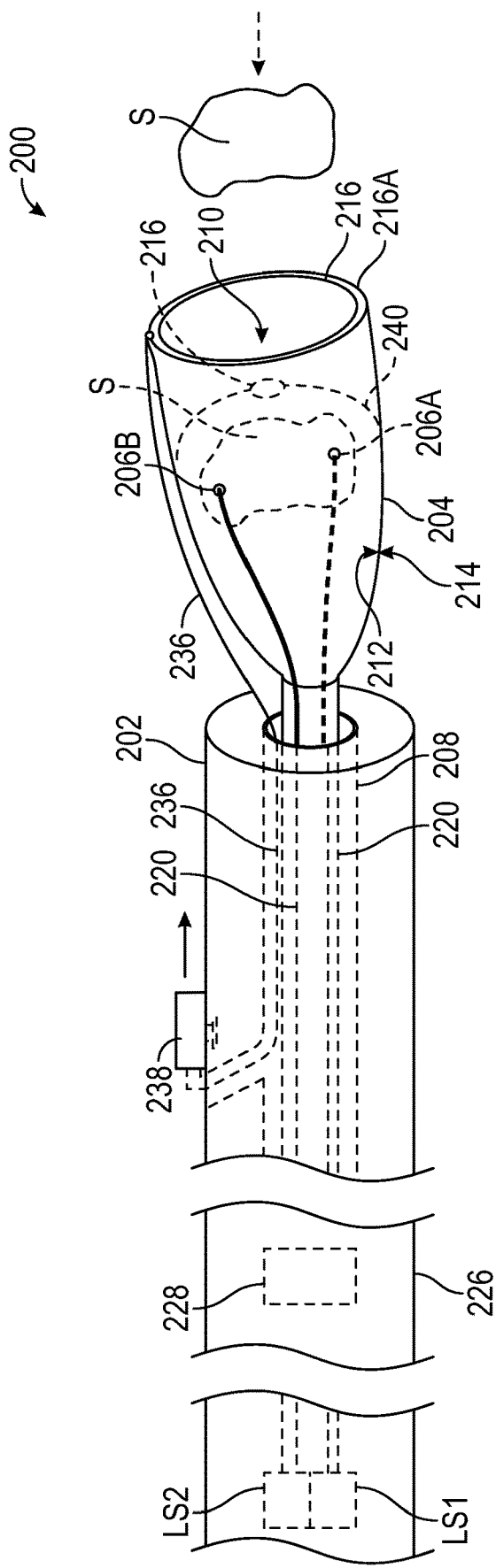
FIG. 2 illustrates a side view of a portion of a second lithotripsy system, in accordance with at least one example.

FIG. 2 shows a side view of a second illustrative example of a laser lithotripsy system 200 with a capture portion 204 shown in a deployed-open position, and the capture portion 204 shown in dotted line in a deployed-closed position 240. The lithotripsy system of FIG. 2 can include features of the lithotripsy system 100 of FIG. 1. Like numbers can represent like elements, therefore, for the sake of brevity all elements may not be described in further detail.

As shown in FIG. 2, the capture portion 204 can be deployed through a lumen 208 of a sheath 202. The capture portion 204 can include a receiving cavity 210. The receiving cavity 210 can have an inner surface 212 and an outer surface 214. In the deployed state, the capture portion 204 can be configured to receive the stone S into the receiving cavity 210 through an opening 216 such that the receiving cavity 210 can at least partially surround the stone S. In some examples, the capture portion 204 can include a layer of compliant material, such as a mesh.

The capture portion 204 can be configured to receive a stone S into the receiving cavity 210 through an opening 216. A closure member 236 can have a distal end portion coupled to the opening 116, and a proximal end portion coupled to an actuator 238 that is actuatable by an operator to close the opening 216, such as by cinching a closure thread 216A. In some examples, the actuator 238 can be located on and coupled to the sheath 202 via a handle coupled to the sheath 202. A handle can provide a user a larger interface for actuating the closure member.

When a stone S to be captured passes through the opening 216 and into the receiving cavity 210, an operator can actuate, such as by sliding an actuator 238, to cause movement of the closure member 236 and thereby a diameter of the opening 216 to be reduced. The opening 216 can be reduced from an open diameter to a less-open or close diameter (e.g., 240, shown in hidden line). Although the actuator 238 is shown as a sliding actuator in FIG. 2, any suitable actuator and motion of the actuator 238 can be provided.

FIG. 2 also shows an illustrative example of a lithotripsy system 200 that can be coupled to multiple laser sources, such as a first laser source LS1 and a second laser source LS2, via at least one laser fiber 220. In some examples, the first laser source LS1 can be individually coupled to the first laser node 206A to communicate a first portion of the laser energy to the receiving cavity 210. The second laser source LS2 can be individually coupled to the second laser node 206B to communicate a second portion of the laser energy to the receiving cavity 210.

In other examples, and as shown in FIG. 3, the first and second laser sources LS1, LS2 can be coupled to more than two laser nodes 306 via a laser coupling 326 including a common manifold 328. In the example of FIG. 2, although two laser nodes are shown, the laser energy from the first and second laser sources LS1, LS2 can be combined and divided in the common manifold 228 in any suitable manner for delivering the laser energy to any number of laser nodes 206 to fragment a stone S. Any of the laser couplings, including any of the manifolds described herein, can be used interchangeably with any of the capture portions, laser nodes, layers, closure members and actuators described herein.

FIG. 3 shows a side view of a third illustrative example of a lithotripsy system 300. The lithotripsy system 300 of FIG. 3 can include features of the lithotripsy system of FIGS. 1 and 2. Like numbers can represent like elements, therefore, for the sake of brevity all elements may not be described in further detail.

As shown in FIG. 3, a capture portion 304 deployable from a lumen 308 of a sheath 302 can be configured to receive a stone S into the receiving cavity 310 through an opening 316. A closure member 336 can include distal end portion coupled to the opening 316, and a proximal end portion coupled to an actuator 338 that is actuatable by an operator to close the opening 316. When a stone S to be captured passes through the opening 316 and into the receiving cavity 310, an operator can actuate, such as by rotating an actuator 338, to cause a layer 318 to be wrapped over the stone S and the opening 316. The layer 318 can include a compliant material, such as a mesh sufficient in size to cover the opening 316.

In some examples, the rotational actuator 338 is configured to be rotated in a range between 45 to 270 degrees to cause the layer 318 to cover the opening 316 and capture a stone S. In a possibly more preferred example, the actuator 338 is configured to rotated in a range between 140-220 degrees to cause the layer 318 to cover the opening 316 and capture a stone S. The actuator 338 need not be a rotational actuator, it is merely provided as one example, any other suitable actuator including a linear sliding actuator can be provided.

FIG. 3 also illustrates an example where the lithotripsy system 300 can be configured to be coupled to multiple laser sources such as a first laser source LS1 and a second laser source LS2. As shown in the example of FIG. 3, the first laser source LS1 and the second laser source LS2 can be operably coupled via a common manifold 338 to a plurality of laser nodes 306, such as a first laser node 306A, a second laser node 306B, a third laser node 306C, a fourth laser node 306D, a fifth laser node 306E, a sixth laser node 306F and a seventh laser node 306G. The common manifold 338 can control and distribute the laser energy from the first and second laser sources LS1, LS2 to any of the laser nodes 306A-G in any combination for communication to the receiving cavity 310 to fragment a stone S. The laser energy can be delivered to the laser nodes through at least one laser fiber 320.

Figure 4:
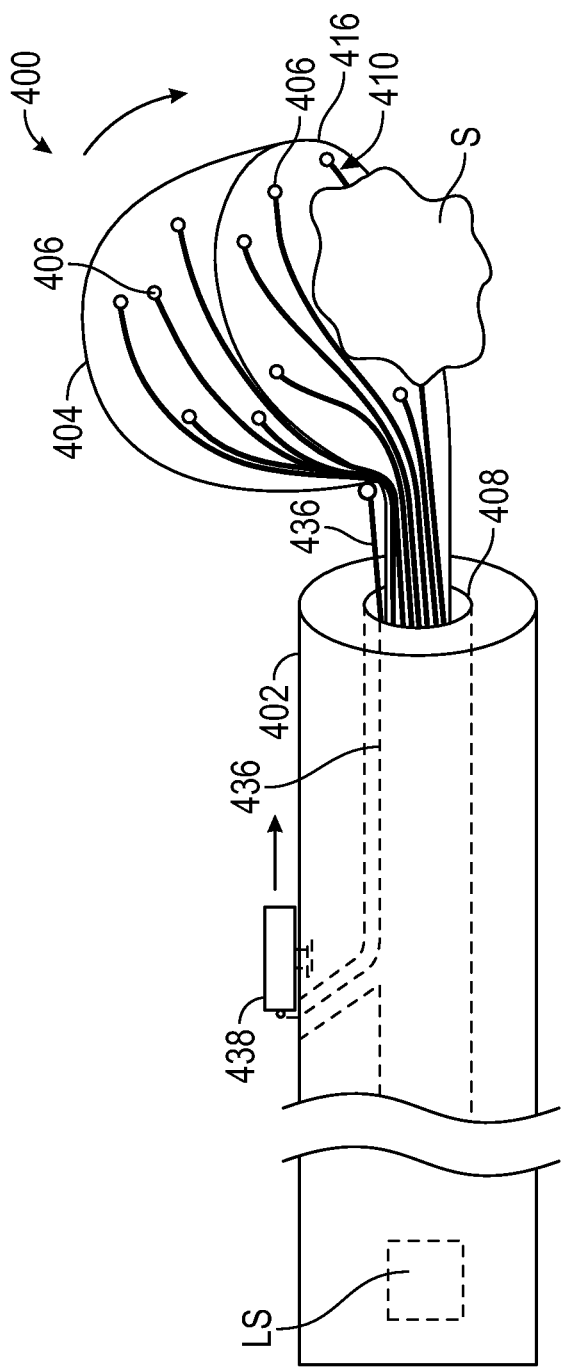
FIG. 4 illustrates a side view of a portion of a fourth lithotripsy system, in accordance with at least one example.

FIG. 4 shows a side view of a fourth illustrative example of a portion of a lithotripsy system 400. The lithotripsy system 400 of FIG. 4 can include features of the lithotripsy systems 100, 200 and 300 of FIGS. 1, 2 and 3. Like numbers can represent like elements, therefore, for the sake of brevity all elements may not be described in further detail.

The lithotripsy system 400 can include a capture portion 404 deployable from a lumen 408 of a sheath 402. The capture portion 404 having a receiving cavity 410 and an opening 416. To capture a stone S, the receiving cavity 410 can be caused to scoop a stone S into an opening 416. For example, when an operator manipulates a scoop actuator 438, a scoop member 436 moves the capture portion 404 in a scooping motion. When a stone S to be captured passes through the opening 416 and into the receiving cavity 410, an operator can actuate, such as by sliding the scoop actuator 438, to cause movement of the closure member 436 which causes a scooping action of the capture portion 404 to occur. Although the actuator 438 is shown as a sliding actuator in FIG. 4, any suitable actuator and motion of the actuator can be provided that causes a scooping motion of the capture portion 404.

At least one laser node 406 can be configured to communicate laser energy received from at least one laser source LS into the receiving cavity 410 the same as or similar to the example laser nodes 106, 206 and 306 described in FIGS. 1, 2 and 3.

Figure 5A:
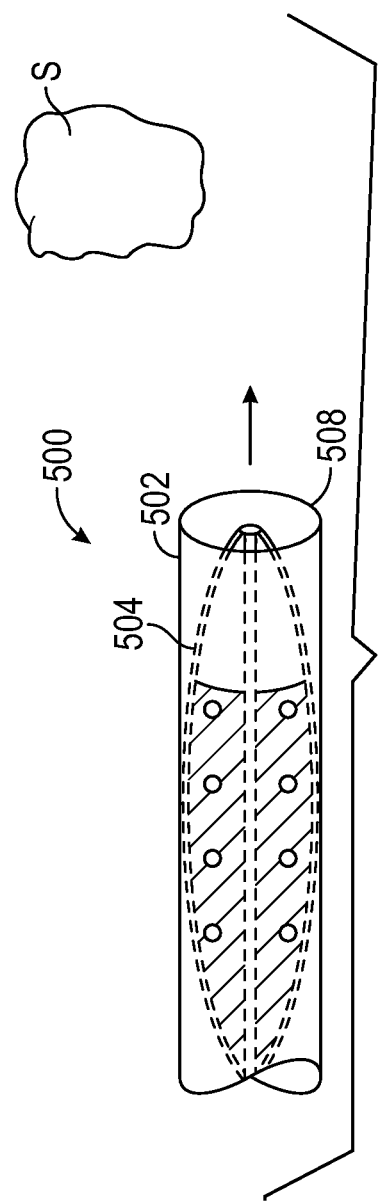
FIG. 5A illustrates a side view of a portion of a fifth lithotripsy system in a stored state, in accordance with at least one example.
Figure 5B:
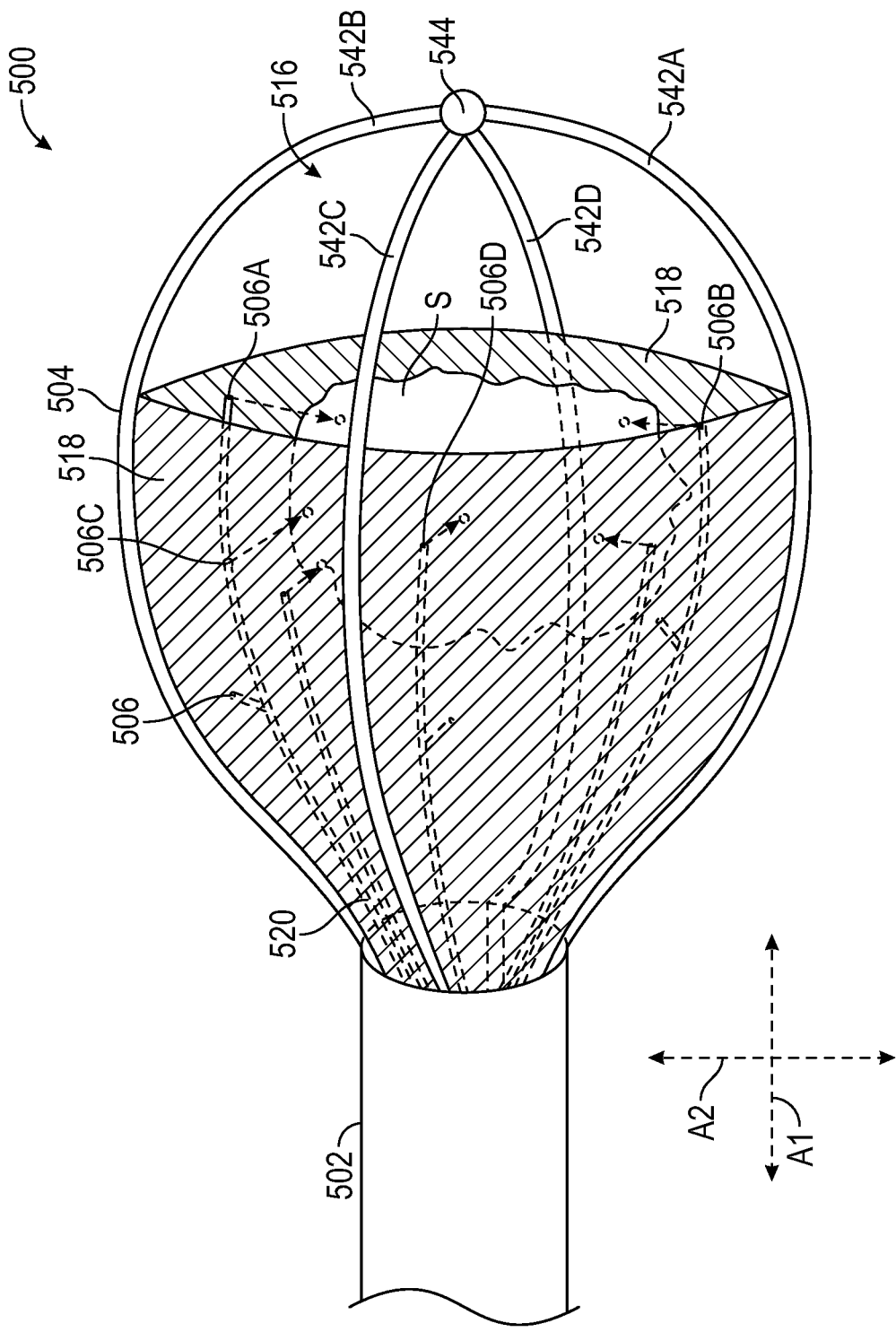
FIG. 5B illustrates a side view of a portion of a fifth lithotripsy system in a deployed state, in accordance with at least one example.

FIG. 5A illustrates a fifth lithotripsy system 500 in a stored state, and FIG. 5B illustrates the fifth lithotripsy system 500 in a deployed state. The lithotripsy system 500 of FIGS. 5A and 5B can include features of the lithotripsy systems 100, 200, 300 and 400 of FIGS. 1, 2, 3 and 4. Like numbers can represent like elements, therefore, for the sake of brevity all elements may not be described in further detail. FIGS. 5A and 5B are described together.

As shown in FIG. 5A, the lithotripsy system 500 can be maintained in a stored state, during delivery through a working channel (WC, FIG. 1) to a treatment site, such as a kidney.

As shown in the deployed or expanded state of FIG. 5B, the lithotripsy system 500 can include a capture portion 504 deployable from a sheath 502 having a lumen 508 (FIG. 5A). The capture portion 504 can have at least one strut 542A, 542B, 542C, 542D and at around a receiving cavity 510, forming a basket. The capture portion 504 can include at least one opening 516 to receive a stone S. The example of FIGS. 5A and 5B depicts four struts 542 that converge at a distal end, however any suitable number of struts 542 for capturing a stone S can be provided. The struts 542A-D can be formed as four individual struts 542A-D that are joined at a distal end coupling such as a hub 544, or the struts 542A-D may be integrally formed with one another or overlap with one another. Suitable materials for the struts 542A-D include resilient and biocompatible materials such as nitinol, spring stainless steel, shape memory polymer, any other suitable shape-memory material, and alloys and combinations of such materials. In some examples, and as shown in FIGS. 5A and 5B, the capture portion 504 can include a layer 518, such as a mesh, woven or non-woven material, to further enclose the receiving cavity 510. In some examples, the layer 518 may be at least partially see-through such that visibility during a procedure is improved. In some examples, the layer 518 may be formed of a thin sheet of pliable, flexible polymeric material such as a film. To improve visibility the film may be a transparent film.

At least one laser node 506 can be coupled to the capture portion 504 to direct laser energy into the receiving cavity 510 to fragment a stone S as described in the lithotripsy system 100 to FIG. 1. The laser node 506 can be coupled to the layer 518 as shown, however, the laser node 506 can be coupled to and/or along the struts 542A-D, such as but not limited to, examples that omit the layer 518. The laser node 506 can receive the laser energy via laser fibers 520.

As shown in FIG. 5B, the capture portion 504 can extend generally along a longitudinal direction A1 and can deploy laterally away from the longitudinal direction A1. The laser nodes 306 can be spaced apart along the capture portion 504 in a variety of ways. For example, a first laser node 506A can be laterally or radially spaced apart from a second laser node 506B along a surface of the capture portion 504 in the deployed state. Radial spacing does not require that the capture portion 504 be frustoconical or have a circular cross-section, although the capture portion 504 can be frustoconical or have a circular cross-section. Rather, a radial direction A2 can indicate a direction extending away from the longitudinal direction A1. In some examples, the longitudinal direction A1 can extend in a proximal-distal direction along a longitudinal axis, and the radial or lateral direction A2 can extend along a radial axis (e.g., A2) perpendicular to the longitudinal axis (e.g., A1), but such geometry is not required.

In another manner of spacing apart the laser nodes 506, a first laser node 506A can be located distal of a third laser node 506C. Further, the laser nodes 506 can be spaced apart in a direction having both a longitudinal component and a lateral or radial component, such as the spacing shown between the first laser node 506A and a fourth laser node 506D.

It is noted that the capture portion 504 of FIGS. 5A and 5B, as well as the other capture portions 104, 204, 304, 404, 604 described herein, can have utility separate from an example including the laser nodes 506. For example, any of the capture portions 104, 204, 304, 404, 504, 604 can be used to collect stones that do not require fragmentation before collection and removal, or the capture portion can be used with other lithotripsy systems.

Figure 6:
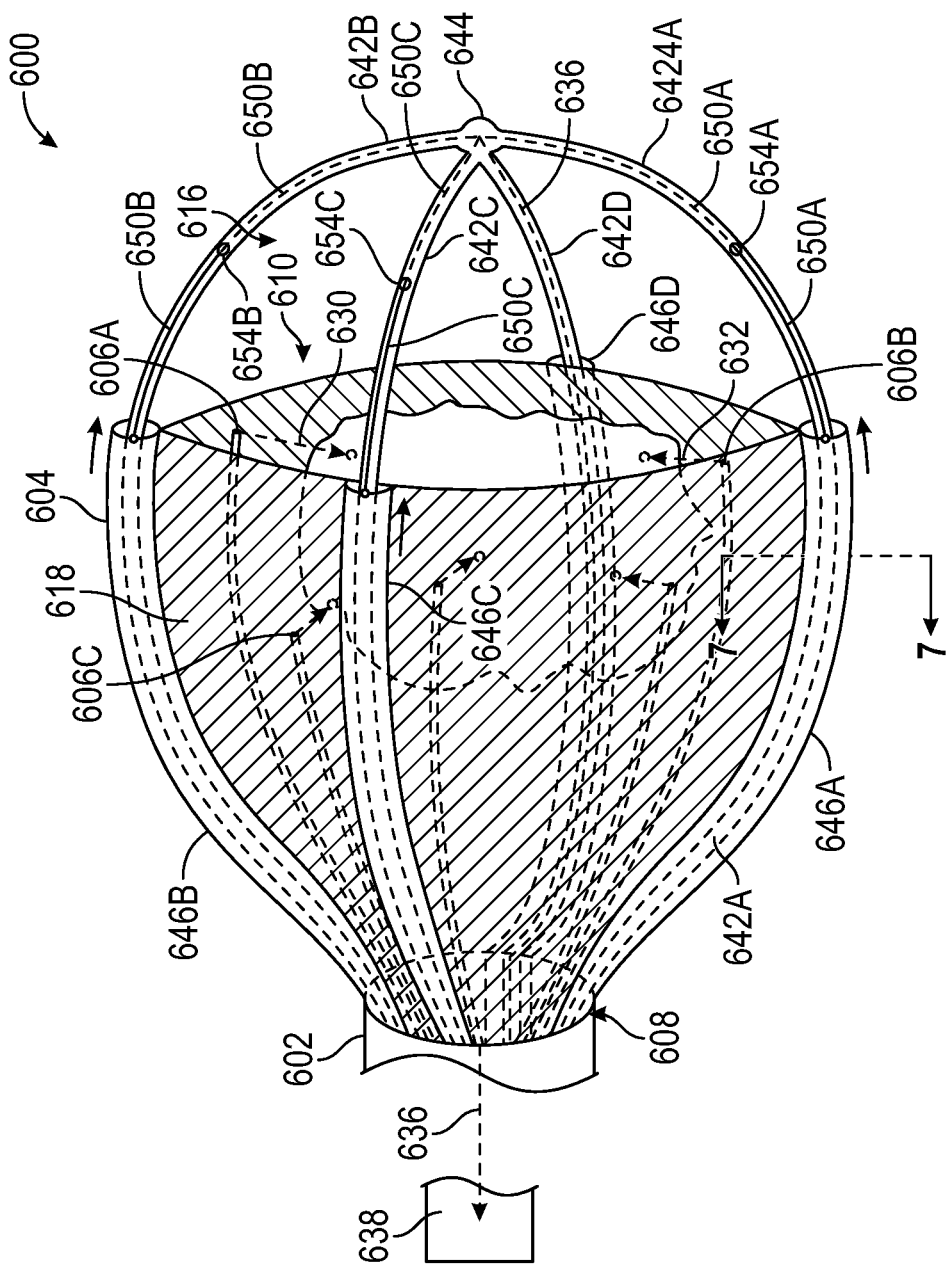
FIG. 6 illustrates a side view of a portion of a sixth lithotripsy system, in accordance with at least one example.

FIG. 6 shows a side view of a sixth illustrative example of a portion of a lithotripsy system 600. The lithotripsy system 600 of FIG. 6 can include features of the lithotripsy systems 100, 200, 300, 400 and 500 of FIGS. 1, 2, 3, 4 and 5. Like numbers can represent like elements, therefore, for the sake of brevity all elements may not be described in further detail.

As shown in a deployed state of FIG. 6, the lithotripsy system 600 can include a capture portion 604 deployable from a sheath 602 having a lumen 608. The capture portion 604 can be similar to the capture portion 504 of FIGS. 5A and 5B, having at least one strut 642A-D and at least one opening 616, forming a receiving cavity 610, such as a basket. The capture portion 604 can include a layer 618, such as a mesh, woven or non-woven material, to further enclose the receiving cavity 610.

The lithotripsy system 600 of FIG. 6 is similar to the system 500 of FIGS. 5A and 5B, however, the system of FIG. 6 can also include features to at least partially close the opening 616 and thereby further confine the stone S. When an operator actuates an actuator 638, such as actuator 238 in FIG. 2, a closure member 636 having a proximal end portion coupled to the actuator 638 and a distal end portion coupled to the layer 618 can be configured to move the layer 618 to reduce size of the opening 616. For example, the closure member 636 can cause the layer 618 to move along the struts 642A-D, such as by sliding distally along the struts 642A-D, to close the opening 616. To close the opening 616 the layer 618 can slide distally when the actuator 638 is actuated. The actuator 638 can be any type of actuator, such as the sliding type actuator 238 shown in FIG. 2.

Figure 7:
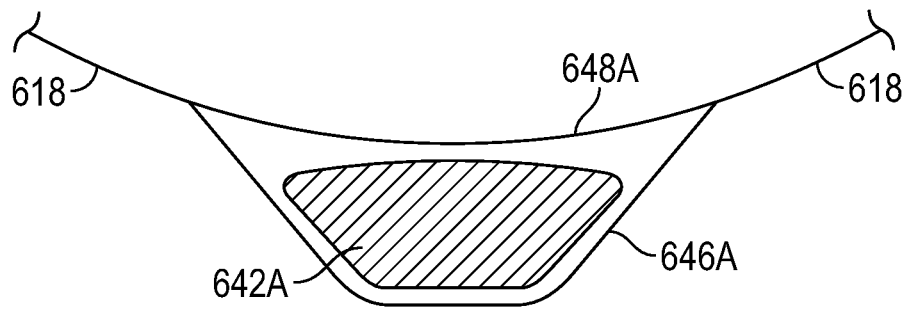
FIG. 7 illustrates of a cross-sectional view of a portion of the sixth lithotripsy system taken along line 7-7 in FIG. 6, in accordance with at least one example.

To slidably couple the layer 618 to the strut 642A-D, the capture portion 604 can include a sleeve 646A-D located around one or more of the struts 642A-D. The sleeves 646A-D can be integrally woven with the layer 618 or attached to the layer 618. FIG. 7 shows a cross-sectional view through a first sleeve 646A and a first strut 642A taken along line 7-7 in FIG. 6. As shown in FIG. 7, the first sleeve 646A is arranged relative to the first strut 642A to slide along the first strut 642A.

One or more laser nodes 606, 606A-D can communicate the laser energy received from at least one laser source (LS, LS1, LS2; FIGS. 1-4) to the receiving cavity 610. In some examples, the system 600 can communicate a first portion of the laser energy from the first laser node 606A towards the receiving cavity 610 along a first path 630 and a second portion of the laser energy from the second laser node 606B towards the receiving cavity 610 along a second path 632 that is different from the first path 630.

In some examples, the system 600 can be selectably controllable. For example, if the operator desires to target application of the laser energy to a particular portion of the stone S, the system 600 can be configured to direct the laser energy to specified laser nodes, such as first laser node 606A and third laser node 606C. The laser nodes 606 can direct laser energy to multiple points on the exterior surface of a stone S concurrently or in a staggered or serial manner. In some examples, the dispersed nature of the laser nodes 606 enables selective, targeted application of energy. For example, the laser energy can be applied on only one side or to one section, or to certain sections of a stone S, depending on the characteristics of the stone S or the operator's preferences. This targeted application of energy can speed up the fracture process to shorten procedure time.

In some examples, the system 600 is selectably controllable to deliver at least a portion of the laser energy through the first laser node 606A, through the second laser node 606B, or through both the first laser node 606A and the second laser node 606B.

Although the illustrative examples show a plurality of laser nodes 606A-D, in some examples, a single laser node (any of 606A-D) can be coupled to a capture portion 604. Such a single laser node can be configured to communicate the laser energy towards the receiving cavity 610 while the capture portion 604 retains the stone S and the resulting stone fragments.

Figure 8:
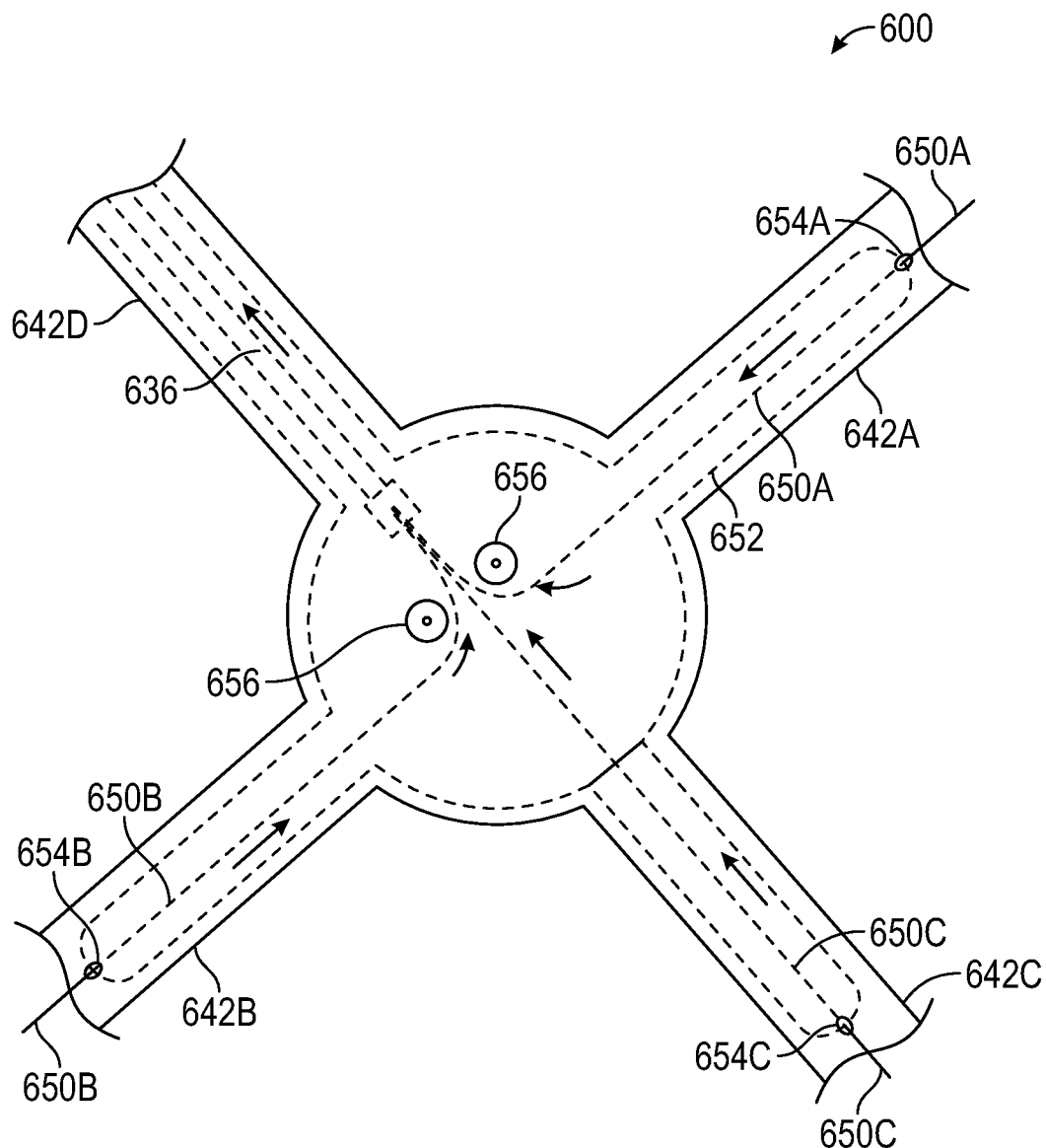
FIG. 8 illustrates a plan view of a distal portion of the sixth lithotripsy system of FIG. 6, in accordance with at least one example.

FIG. 8 shows a plan view of the distal end portion of the sixth lithotripsy system 600 of FIG. 6 in the deployed state. FIGS. 6 and 8 are described together. The distal end portion of the capture portion 604 can include a hub 644. The struts 642A-D can extend laterally and proximally away from the hub 644. As shown in FIG. 6, the closure member 636 can be attached to an actuator 638 at a proximal end portion. The closure member can be coupled to the layer 618 via at least one thread 650A, 650B, 650C such as a wire, cable, cord, string, strap, belt or filament at a distal end portion.

FIG. 8 shows a plan view of the hub 644, a portion of the struts 642A-C, the closure member 636 and the threads 650A-C. The closure member 636 can be coupled to or integrally formed with the at least one thread 650A-C such that when the closure member 636 is pulled proximally, a distal end portion of the threads 650A-C, which are coupled to the closure member 636, move and thereby cause the layer 618 to move distally. The hub 644 can include at least one thread guide 656 configured to route at least one of the threads 650A, B.

As shown in FIG. 8 with support from FIG. 6, the distal end portions of the threads 650A-C can be located in the channel 652A-C within the struts 642A-C and can attached to the closure member 636 proximate the hub 644. The threads 650A-C can extend proximally through the channels 652A-C in each of the respective struts 642A-C. The threads 650A-C can pass laterally out of the respective channels 652A-C, exiting the struts 542A-C through a hole 654A-C in each of the respective struts 642A-C. The threads 65A-C can exit the struts 642A-642C along an intermediate portion of the threads 650A-C to exit the respective strut 642A-C. The proximal portion of the threads 650A-C can be located external to the struts 642A-C and can attach to the respective sleeve 648A-C or to the layer 618 proximate the respective sleeve 648A-C. In this arrangement, proximal movement of the closure member 636 when actuator 638 is actuated, causes distal movement of the threads 650A-C along strut 642D, thereby applying a force to the layer 618 to move the layer 618 distally. The result of actuating actuator 638 thus causes the opening 616 to be at least partially closed (e.g., opening 616 size can be reduced from a receiving state to a captured state).

The threads 650A-C are shown in merely one arrangement. In some examples, the threads 650A-C can be located internal to the capture portion 604 within the receiving cavity 610, or the threads 650A-C can be located external to the capture portion 604, outside the receiving cavity 610.

Figure 9A:
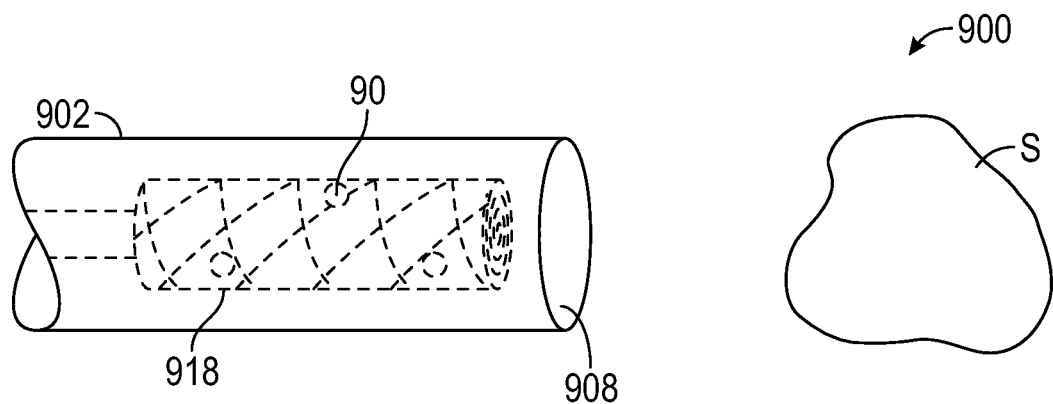
FIG. 9A illustrates a side view of a portion of a seventh lithotripsy system in a stored state, in accordance with at least one example.
Figure 9B:
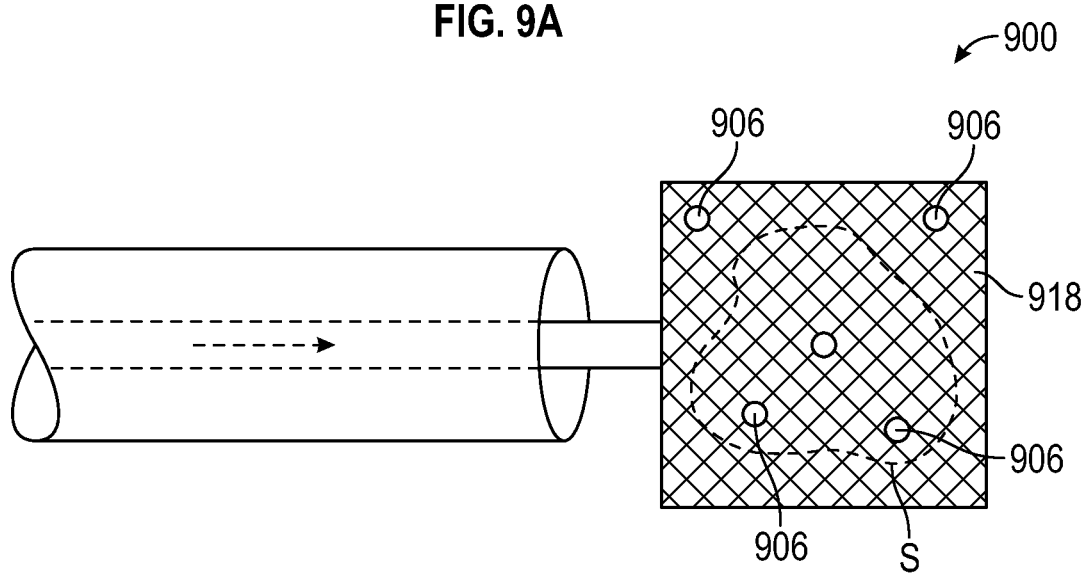
FIG. 9B illustrates a side view of a portion of the seventh lithotripsy system in a deployed state, in accordance with at least one example.

FIG. 9A illustrates a side view of a portion of a seventh lithotripsy system 900 in a stored state. FIG. 9B illustrates a side view of a portion of the seventh lithotripsy system 900 in a deployed state. The lithotripsy system of FIGS. 9A and 9B can include features of the lithotripsy systems 100, 200, 300, 400, 500, 600 of FIGS. 1, 2, 3, 4, 5 and 6. Like numbers can represent like elements, therefore, for the sake of brevity all elements may not be described in further detail.

In an alternative to providing a laser lithotripsy system including a capture device, such as a bag or basket, the laser nodes 906 in the system 900 can be coupled to a layer 918, such as a sheet or mesh that can be positioned on the surface of a stone S to apply laser energy to the surface of the stone S at multiple locations, without capturing the stone S. As shown in the stored state of FIG. 9A, the layer can be rolled or otherwise made compact within the lumen 902 of a sheath 908 for delivery through a working channel (WC, FIG. 1) of a scope or other instrument. As shown in the stored state of FIG. 9B, the layer 918 can be deployed by being moved distally and expanded, to provide a layer 918 of spaced apart laser nodes 906 that can be applied to a stone S.

In some examples, communication of the laser energy to the stone S through the laser nodes in any of the examples described herein may be constant or variable. In a variable example, the laser lithotripsy system can be configured to provide a variable energy intensity laser output. For example, a lower energy intensity can be used, such as for providing an "aiming" beam or for treating soft (e.g., non-calcified) tissue, and one or more higher energy intensities can be used for providing a "treatment" beam, such as for hard (e.g., calcified) tissue or stones. Multiple higher energy intensity treatment beam levels can be provided, such as on a pulse-by-pulse or target location dependent basis, such as to establish, adjust, or tune a desired treatment pulse energy intensity to a specified level.

Further, in some examples, instead of communication of the laser energy to the stone S through the first and second laser nodes simultaneously, the application of energy can be staggered. The first and second nodes can be activated serially or in an overlapping pattern such that at certain points in time only the first laser node or the second laser node is delivering energy to the stone S. In such a staggered example, at a given point in time, the first portion of the laser energy that is received by the first laser node can be the total laser energy produced by at least one laser source (e.g., LS, FIG. 1).

Figure 10:
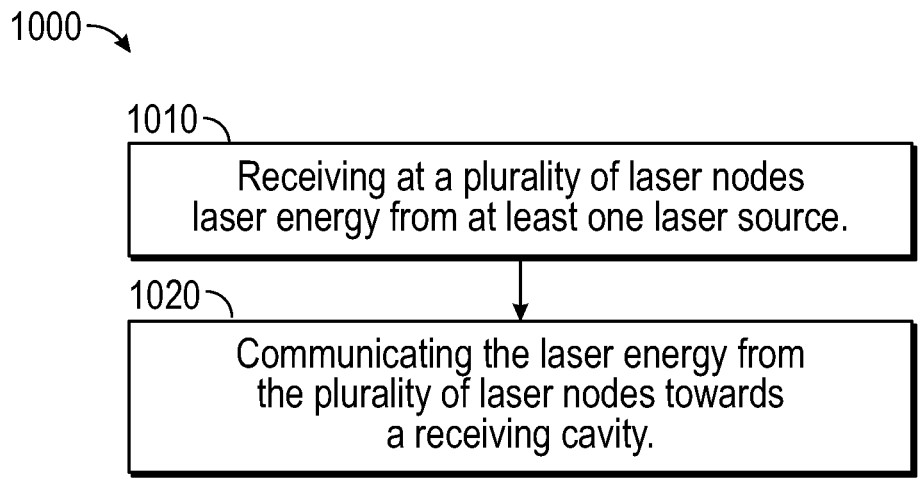
FIG. 10 illustrates a flow chart illustrating a method of transmitting laser energy in a laser therapy device, such as a laser lithotripter, in accordance with at least one example.

FIG. 10 is a flow chart illustrating a method 1000 of transmitting laser energy in a laser therapy device, such as a laser lithotripter. The laser energy can be received from one or more laser sources. The method 1000 can be performed using any of the laser lithotripsy systems described herein in FIGS. 1-4, 5A, 5B, 6-8, 9A and 9B. However, the method 1000 can also be used with other laser lithotripters or other laser therapy devices or procedures. Likewise, the systems of FIGS. 1-4, 5A, 5B, 6-8, 9A and 9B can be used with other methods.

Step 1010 can include receiving at a plurality of laser nodes, the laser energy from the one or more laser sources operably couplable to the plurality of laser nodes. The laser nodes can be arranged in a spaced apart relationship along a surface of a capture portion. The surface can form a receiving cavity for receiving a stone.

Step 1020 can include communicating the laser energy from the plurality of laser nodes towards the receiving cavity. In some examples the plurality of laser nodes includes a first laser node and a second laser node, where the first laser node is located distal of the second laser node, and/or the first laser node and the second laser node are laterally or radially spaced apart along the surface of the capture portion.

In some examples, communicating the laser energy through plurality of laser nodes in step 1020 can include communicating a first portion of the laser energy from the first laser node towards the receiving cavity along a first path and communicating a second portion of the laser energy towards the receiving cavity along a second path that is different from the first path. Further, communicating any portion of the laser energy from an laser node can include deflecting, reflecting, refracting or diffracting the laser energy towards the receiving cavity.

In some examples, communicating the laser energy through the plurality of laser nodes in step 1020 can include selectively controlling delivery of the first portion of the laser energy from the first laser node and selectively controlling delivery of the second portion of the laser energy from the second laser node, wherein the first portion of the laser energy is greater than the second portion of the laser energy. This selective application of laser energy can be applied to a lithotripsy system having any number of laser nodes. Further, in some examples, the second portion of the laser energy can equal zero, such that the laser energy is delivered through the first laser node, but not through the second laser node, in order to provide targeted delivery of the laser energy to certain portions of the stone. This selective application can be applied to any number of laser nodes. The portion of laser energy delivered to the nodes can be varied such that any one or more of the following can occur: one node may receive all of the laser energy; a plurality of nodes can receive a divided portion of the laser energy, and one or more laser nodes can receive no laser energy.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

VARIOUS NOTES AND EXAMPLES

Example 1 is a laser lithotripsy system to deliver laser energy from one or more laser sources to a mobile calculus, the system comprising: a capture portion configured to be movable from a stored state to a deployed state, wherein in the deployed state, the capture portion is configured to at least partially surround the mobile calculus; and a first laser node and a second laser node coupled to the capture portion, the first and second laser nodes configured to deliver the laser energy to the mobile calculus, and wherein the first laser node is spaced apart from the second laser node.

In Example 2, the subject matter of Example 1 includes, wherein in the deployed state, the capture portion comprises a receiving cavity and an opening to receive the mobile calculus into the receiving cavity, and wherein the first laser node and the second laser node are configured to direct the laser energy inward from a surface of the capture portion towards the receiving cavity.

In Example 3, the subject matter of Examples 1-2 includes, wherein the first laser node is located distal of the second laser node in the deployed state.

In Example 4, the subject matter of Examples 1-3 includes, wherein the first laser node and the second laser node are radially spaced apart along a surface of the capture portion in the deployed state.

In Example 5, the subject matter of Examples 1-4 includes, wherein the first laser node is configured to deliver a first portion of the laser energy to the mobile calculus, and wherein the second laser node is configured to deliver a second portion of the laser energy to the mobile calculus, and wherein the system is selectably controllable to deliver at least a portion of the laser energy through the first laser node, through the second laser node, or through both the first laser node and the second laser node.

In Example 6, the subject matter of Examples 1-5 includes, wherein the capture portion comprises a deployable strut actuatable to deliver the capture portion to a treatment site through a working channel.

In Example 7, the subject matter of Examples 1-6 includes, wherein the capture portion comprises a mesh.

In Example 8, the subject matter of Examples 1-7 includes, wherein the first laser node is configured to at least one of deflect, reflect, refract or diffract at least a portion of the laser energy.

In Example 9, the subject matter of Examples 1-8 includes, wherein the first laser node comprises a first reflective surface configured to deflect the first portion of the laser energy.

Example 10 is a method of transmitting laser energy in a laser therapy device, the laser energy received from one or more laser sources, the method comprising: receiving at a plurality of laser nodes, the laser energy from the one or more laser sources operably couplable to the plurality of laser nodes, wherein the plurality of laser nodes are arranged in a spaced apart relationship along a surface of a capture portion, and wherein the surface forms a receiving cavity; and communicating the laser energy from the plurality of laser nodes towards the receiving cavity.

In Example 11, the subject matter of Example 10 includes, wherein the plurality of laser nodes includes a first laser node and a second laser node, wherein the first laser node is located distal of the second laser node when the capture portion is in a deployed state.

In Example 12, the subject matter of Examples 10-11 includes, wherein the plurality of laser nodes includes a first laser node and a second laser node, wherein the first laser node and the second laser node are laterally spaced apart along the surface of the capture portion when the capture portion is in a deployed state.

In Example 13, the subject matter of Examples 10-12 includes, wherein communicating the laser energy through the plurality of laser nodes includes communicating a first portion of the laser energy from the first laser node towards the receiving cavity along a first path and communicating a second portion of the laser energy from the second laser node towards the receiving cavity along a second path that is different from the first path.

In Example 14, the subject matter of Example 13 includes, wherein communicating the first portion of the laser energy from the first laser node includes deflecting, reflecting, refracting or diffracting the first portion of the laser energy.

In Example 15, the subject matter of Examples 10-14 includes, wherein communicating the laser energy through the plurality of laser nodes includes communicating a first portion of the laser energy through the first laser node and communicating a second portion of the laser energy through the second laser node, the method further comprising: selectively controlling delivery of the first portion of the laser energy from the first laser node and selectively controlling delivery of the second portion of the laser energy from the second laser node, wherein the first portion of the laser energy is greater than the second portion of the laser energy.

In Example 16, the subject matter of Example 15 includes, wherein the second portion of the laser energy equals zero.

Example 17 is a laser therapy system to deliver laser energy from one or more laser sources to a mobile calculus, the system comprising: a capture portion configured to at least partially surround the mobile calculus in a deployed state; and a first laser node and a second laser node coupled to the capture portion, wherein the first laser node is configured to apply a first portion of the laser energy to a first location on the mobile calculus, and wherein the second laser node is configured to apply a second portion of the laser energy to a different second location on the mobile calculus.

In Example 18, the subject matter of Example 17 includes, wherein the first laser node is spaced apart from the second laser node.

In Example 19, the subject matter of Examples 17-18 includes, wherein the capture portion is movable from a stored state to the deployed state, and in the deployed state, the capture portion comprises a receiving cavity and an opening to receive the mobile calculus into the receiving cavity, and wherein the first laser node and the second laser node are configured to direct the laser energy inward from a surface of the capture portion towards the receiving cavity.

In Example 20, the subject matter of Examples 17-19 includes, wherein the first laser node is located distal of the second laser node in the deployed state.

In Example 21, the subject matter of Examples 17-20 includes, wherein the first laser node and the second laser node are laterally spaced apart along a surface of the capture portion in the deployed state.

In Example 22, the subject matter of Examples 17-21 includes, wherein the system is selectably controllable to deliver the laser energy through the first laser node, through the second laser node, or through both the first laser node and the second laser node.

In Example 23, the subject matter of Examples 17-22 includes, wherein the capture portion comprises a deployable strut actuatable to deliver the capture portion to a treatment site through a working channel.

Example 24 is at least one machine-readable medium including instructions that, when executed by processing circuitry, cause the processing circuitry to perform operations to implement of any of Examples 1-23.

Example 25 is an apparatus comprising means to implement of any of Examples 1-23.

Example 26 is a system to implement of any of Examples 1-23.

Example 27 is a method to implement of any of Examples 1-23.

What is claimed is:

1. A laser lithotripsy system to deliver laser energy from one or more laser sources to a mobile calculus, the system comprising:
    a capture portion configured to be movable from a stored state to a deployed state, wherein in the deployed state, the capture portion includes an inner surface that is configured to at least partially surround the mobile calculus; and
    a first laser node and a second laser node arranged along the inner surface of the capture portion and each having a corresponding laser fiber, the first and second laser nodes comprising a redirection element configured to deliver the laser energy to the mobile calculus by redirecting the laser energy from a direction extending along a respective laser fiber thereof toward the mobile calculus within the capture portion, and wherein the first laser node is spaced apart from the second laser node.

2. The system of claim 1, wherein in the deployed state, the capture portion comprises a receiving cavity and an opening to receive the mobile calculus into the receiving cavity.

3. The system of claim 1, wherein the first laser node is located distal of the second laser node in the deployed state.

4. The system of claim 1, wherein the first laser node and the second laser node are radially spaced apart along a surface of the capture portion in the deployed state.

5. The system of claim 1, wherein the first laser node is configured to deliver a first portion of the laser energy to the mobile calculus, and wherein the second laser node is configured to deliver a second portion of the laser energy to the mobile calculus, and wherein the system further comprises a common manifold configured to control and deliver at least a portion of the laser energy through the first laser node, through the second laser node, or through both the first laser node and the second laser node.

6. The system of claim 1, wherein the capture portion comprises a deployable strut actuatable to deliver the capture portion to a treatment site through a working channel.

7. The system of claim 1, wherein the capture portion comprises a mesh.

8. The system of claim 1, wherein the first laser node is configured to at least one of deflect, reflect, refract or diffract at least a portion of the laser energy.

9. The system of claim 1, wherein the first laser node comprises a first reflective surface configured to deflect the first portion of the laser energy.

10. The laser lithotripsy system of claim 1, further comprising at least a third laser node for delivering the laser energy to the mobile calculus, wherein the first, second and at least third laser nodes deliver the laser energy to different locations on the mobile calculus.

11. A laser therapy system to deliver laser energy from one or more laser sources to a mobile calculus, the system comprising:
    a capture portion configured to at least partially surround the mobile calculus in a deployed state; and
    a first laser node and a second laser node arranged along an inner surface of the capture portion and each having a corresponding laser fiber for delivering laser energy, the first and second laser nodes comprising a redirection element configured to deliver the laser energy to the mobile calculus by redirecting the laser energy from a direction extending along a respective laser fiber thereof toward the mobile calculus within the capture portion, wherein the first laser node is configured to apply a first portion of the laser energy to a first location on the mobile calculus, and wherein the second laser node is configured to apply a second portion of the laser energy to a different second location on the mobile calculus.

12. The system of claim 11, wherein the first laser node is spaced apart from the second laser node.

13. The system of claim 11, wherein the capture portion is movable from a stored state to the deployed state, and in the deployed state, the capture portion comprises a receiving cavity and an opening to receive the mobile calculus into the receiving cavity.

14. The system of claim 11, wherein the first laser node is located distal of the second laser node in the deployed state.

15. The system of claim 11, wherein the first laser node and the second laser node are laterally spaced apart along a surface of the capture portion in the deployed state.

16. The system of claim 11, wherein the system further comprises a common manifold configured to control and deliver the laser energy through the first laser node, through the second laser node, or through both the first laser node and the second laser node.

17. The system of claim 11, wherein the capture portion comprises a deployable strut actuatable to deliver the capture portion to a treatment site through a working channel.

18. The laser therapy system of claim 11, further comprising at least a third laser node for delivering the laser energy to the mobile calculus, wherein the first, second and at least third laser nodes deliver the laser energy to different locations on the mobile calculus.

19. A laser lithotripsy system to deliver laser energy from one or more laser sources to a mobile calculus, the system comprising:
a capture portion configured to be movable from a stored state to a deployed state, wherein in the deployed state, the capture portion comprises a receiving cavity configured to at least partially surround the mobile calculus; and
a first laser node and a second laser node arranged along an inner surface of the capture portion and each having a corresponding laser fiber, the first and second laser nodes comprising a redirection element configured to deliver the laser energy to the mobile calculus by redirecting the laser energy from a direction extending along a respective laser fiber, inward from the inner surface of the capture portion, and toward the mobile calculus in the receiving cavity of the capture portion, and wherein the first laser node is spaced apart from the second laser node.

20. The system of claim 19, wherein in the deployed state, the capture portion comprises an opening to receive the mobile calculus into the receiving cavity.

21. The system of claim 19, wherein the first laser node is located distal of the second laser node in the deployed state.

22. The system of claim 19, wherein the first laser node and the second laser node are radially spaced apart along a surface of the capture portion in the deployed state.

23. The system of claim 19, wherein the first laser node is configured to deliver a first portion of the laser energy to the mobile calculus, and wherein the second laser node is configured to deliver a second portion of the laser energy to the mobile calculus, and wherein the system is selectably controllable to deliver at least a portion of the laser energy through the first laser node, through the second laser node, or through both the first laser node and the second laser node.

24. The system of claim 19, wherein the capture portion comprises a deployable strut actuatable to deliver the capture portion to a treatment site through a working channel.

25. The laser lithotripsy system of claim 19, further comprising at least a third laser node for delivering the laser energy to the mobile calculus, wherein the first, second and at least third laser nodes deliver the laser energy to different locations on the mobile calculus.

* * * * *